United States Patent [19]

Buckl et al.

[11] 4,105,467

[45] Aug. 8, 1978

[54] PROCESS FOR TWO-STAGE DIGESTION OF NATURAL PRODUCTS CONTAINING XYLANE, IN ORDER TO OBTAIN XYLOSE

[75] Inventors: Hans Buckl, Freising-Tümtenhausen; Bernd Brenner, Moosburg; Wolfgang Eisenschmid, Au, Hallertau, all of Germany

[73] Assignee: Sud-Chemie Aktiengesellschaft, Munich, Germany

[21] Appl. No.: 729,231

[22] Filed: Oct. 4, 1976

[30] Foreign Application Priority Data

Oct. 8, 1975 [DE] Fed. Rep. of Germany ....... 2545111

[51] Int. Cl.$^2$ ........................ C13K 13/00; C13K 1/02; C07C 29/00

[52] U.S. Cl. .......................................... 127/37; 536/1; 568/863

[58] Field of Search ...................... 127/37; 260/635 C; 536/1

[56] References Cited

U.S. PATENT DOCUMENTS

| | | | |
|---|---|---|---|
| 2,697,701 | 12/1954 | Heritage et al. | 536/1 |
| 3,579,380 | 5/1971 | Friese | 536/1 |
| 3,970,712 | 7/1976 | Friese | 260/635 C |
| 3,990,904 | 11/1976 | Friese et al. | 260/635 C |

*Primary Examiner*—Johnnie R. Brown

*Attorney, Agent, or Firm*—Burgess, Dinklage & Sprung

[57] ABSTRACT

An improvement in a process for the production of xylose or xylitol wherein a vegetable material is contacted with a basic substance and the solid residue is thereafter treated with an acid, the improvement resides in the use of stone nut shells, in employing a two-stage digestion initially with a 1.5–6 molar alkali metal hydroxide solution at 10°–50° C and thereafter diluting the digestion mass to 0.75 molar or less and digesting at a temperature of at least 60° C.

8 Claims, No Drawings

PROCESS FOR TWO-STAGE DIGESTION OF NATURAL PRODUCTS CONTAINING XYLANE, IN ORDER TO OBTAIN XYLOSE

BACKGROUND OF THE INVENTION

1. Field of the Invention

This invention relates to an improvement in a process for the production of xylose or xylitol wherein a vegetable material is contacted with a basic substance and the solid residue is thereafter treated with an acid. The improvement resides:

in the use of stone nut shells, in employing a two-stage digestion initially with a 1.5 to 6 molar alkali metal hydroxide solution at 10° to 50° C, thereafter diluting the digestion mass to 0.75 molar or less, and digesting at a temperature of at least 60° C.

2. Discussion of the Prior Art

D-(+)-xylose and its hydrogenation product, xylitol, are of not inconsiderable technical importance. Xylose can for example be used in the foodstuffs industry for various purposes, while xylitol has proved a very valuable sweetening agent for diabetics. As the starting material for the technical production of xylose there are used almost solely deciduous types of wood, such as beech and chestnut. The yields are about 10–12% (cf.e.g. German Patent Specification No. 912,440). A serious disadvantage of this process lies in that the residual wood substance, the "cellolignin," could not hitherto be put to any useful technical application, and that with this process only moderate xylose yields are obtained.

The obtaining of xylose from oat husks is already known from German Patent Specification No. 834,079. In this process the oat husks are heated with 0.08% ammonia to boiling point, or extracted with benzol -alcohol. Then follows the usual pressure hydrolosis with 0.2 to 0.5% $H_2SO_4$ at 125° C. No further processing takes place. In the preliminary treatment with $NH_3$, 4kg $NH_3$ in an 0.08% solution are used for every 1,000 kg oat husks. However in order to separate off the acetic acid, 17 kg $NH_3$ are necessary. Furthermore under the conditions mentioned in the German patent specification hardly any separation-off and hence elimination of the acetic acid, which makes up about 6% by weight of the oat husks, may take place.

Starting from this process there were proposed in German Offenlegungsschriften Nos. 2,358,407 and 2,358,472 processes for the production of xylose solutions by the digestion or pulping of deciduous wood or oat shells with a basic agent and treatment of the solid residue obtained with mineral acid. These processes which are characterised in that as the basic agent alkali hydroxide is used, in the first place permit the complete utilisation of the starting material and secondly give a higher xylose yield.

When using desiduous wood or oat husks as the starting material the applicant has found in both these cases that the alkali hydroxide solution used for the pulping or digesting in the first stage, only permitted a relatively low concentration. If for example a sodium hydroxide solution is used then its concentration amounts to no more than 4% by weight (= 1-molar solution) otherwise, with the necessarily high digestion temperatures, not only is the bound acetic acid removed but also too large a proportion of the lignin and the hemicelluloses passes into the solution. This means that the xylose yield diminishes with an increasing disintegration of the residue with diluted mineral acids.

It has now been found that when digesting or pulping hard shellnut type (hereinafter termed "stone nut") shells by the process of German Offenlegungsschrift Nos. 2,358,407 or 2,358,472, the maximum concentration indicated there of the alkali hydroxide solution of 4 percent by weight is not sufficient to effectively split off the bound acetic acid. A thorough-going removal of the bound acetic acid at the stage of the alkaline decomposition is therefore necessary, as the acetic acid would otherwise be split off with mineral acid in the second stage and would interfere with the neutralisation of the mineral acid, so that a considerable consumption of ion exchangers is necessary. Traces of acetic acid furthermore act deleteriously during the subsequent catalytic hydrogenation of xylose to xylitol as they poison the catalyst. In this case therefore a very careful cleaning of the xylose solutions is necessary.

When using an alkali hydroxide solution with a concentration of more than 4% by weight admittedly a more intense removal of the bound acetic acid can be anticipated in the first stage, but according to certain findings with deciduous wood or oat husks, the difficulties indicated above must be reckoned with.

SUMMARY OF THE INVENTION

It has now surprisingly been found that when using stone nut shells as the starting material in the first alkaline processing stage, on the one hand a satisfactory release of the bound acetic acid takes place and on the other hand the pentosanes are still not noticeably decomposed, when the alkali hydroxide solutions are next used at a higher concentration at lower temperatures, whereupon the alkali treatment is completed after diluting the digestion solution at higher temperatures.

The invention therefore relates to a process for two-stage digestion or pulping of natural products containing xylane in order to obtain xylose, wherein the starting material in the first stage is treated with a basic agent and the solid residue obtained is treated in the second stage with dilute mineral acid; the process is characterised in that in the digestion or pulping of stone nut shells, in the first stage, as basic agent, a substantially 1.5 to 3-molar alkali hydroxide solution is caused to act on the stone nut shells at temperatures of about 10° to 50° C in a first step for the splitting off and neutralisation of the acetic acid bond in the stone nut shells, and the alkali treatment is completed after diluting the digestion solution to a molar concentration of less than about 0.75 at temperatures of more than about 60° C.

Examples of stone nut shells are coconut shells, almond shells, the shells of palm nuts, olive stones, date stones, babacu nuts and similar stone nuts. Preferably the stone nut shells are pulverised before the alkali treatment in order to provide satisfactory contact with the digestion solution. Generally speaking the grain sizes of the pulverised stone nut shells lie in the range from about 1 to 5 mm, but naturally greater or smaller grain sizes can be used. As alkali metal hydroxide solutions for economic reasons there are preferably used sodium hydroxide solutions, wherein the above-mentioned concentration of 1.5 to 3 mol/liter corresponds to a concentration of 6 to 12% by weight NaOH. If a potassium hydroxide solution is used then the molar concentrations can be calculated in a corresponding manner on the weight.

Preferably the operation begins from a substantially 1.75 to 2.5 molar, preferably a substantially 2-molar alkali metal hydroxide solution, i.e. in the case of a sodium hydroxide solution from one with substantially 7 to 10, preferably about 8% by weight NaOH.

Preferably the concentrated alkali metal hydroxide solution is allowed to act on the stone nut shells at room temperature at about 40° C for about ½ to 3 hours, preferably about 1 to 2 hours, wherein the period of action can naturally be made shorter the higher the temperature and/or the concentration of the alkali hydroxide solution. The optimum concentrations, temperatures and periods of action can easily be determined by routine tests.

After the dilution of the alkaline digestion solution to a molar concentration of less than about 0.75 (corresponds to a NaOH concentration of less than about 3% by weight) the alkaline digestion is completed at temperatures of more than about 60° C. If operations are carried out at normal pressure, then the alkali hydroxide solution is preferably 0.15 to 0.2 molar (corresponding to 0.6 to 0.8% by weight NaOH), the operation being generally carried out at the boiling point of the solution.

If higher pressure is used, then the molar concentration of the alkali hydroxide solutions can advantageously be about 0.1 to 0.4, preferably about 0.13 to 0.25, in particular 0.15. In this case the pressure is preferably up to 3 atmospheres gauge pressure, the temperature preferably up to 125° C. The pressure is generally produced autogeneously in the autoclave.

By the alkali treatment in the first stage of the operation the bound acetic acid present in the stone nut shells is split-off and neutralised. Furthermore the crystallisation-restricting nitrogen-containing substances and other accompanying substances, regarding whose nature nothing is yet known, pass into solution, while the pentosan is not attacked by the alkali hydroxide. The acetic acid can be distilled-off after the acidulation of the alkaline digestion solution, and if desired, can be obtained from the distillate by extraction with a suitable solvent. In addition to the concentration of the alkaline digestion solution being important, its quantity is also important, i.e. the alkali hydroxide must completely neutralise the bound acetic acid, for which reason in general about 1 to 2 mol, preferably about 1.1 to 1.2 mol alkali hydroxide per mol of bound acetic acid, are used. The quantity of bound acetic acid can easily be determined by a test digestion operation.

The stone nut shells treated in the first stage are digested after separation-off (e.g. filtration or extraction) of the digestion solution which contains the acetic acid as alkali acetate, in known manner with a diluted mineral acid at higher temperature with or without pressure.

In this connection it is possible to operate for example with $H_2SO_4$, HCl or HBr, e.g. in water, preferably with $H_2SO_4$. When working without pressure there is preferably used 1.5 to 6.0% by weight HCl or HBr or 1.5 to 6.0% by volume $H_2SO_4$. With the preferred pressure digestion at about 2.5 to 4 atmospheres gauge pressure there is preferably used 0.4 to 1.5% by weight HCl or HBr or even better 0.4 to 1.0% by volume $H_2SO_4$. The ratio of liquid to solid should preferably be 4:1 to 7:1 volumes/weight of solid. The time required is about 1 to 2 hours when operating without pressure and about 30 minutes to 1 hour when operating under pressure.

After the end of the second stage of the operation the batch is filtered or extracted. The liquid can be processed to xylose or directly to xylitol. If in the second stage sulphuric acid has been used, then it is possible to neutralise with barium carbonate, calcium oxide or preferably with calcium carbonate in the calculated quantity. There is then obtained after removal of the residue a xylose solution, which can be reduced immediately to xylitol while hitherto for removing acetic acid the solution had to be thickened or passed over an ion exchanger. The yield of pure xylose is up to 24%.

By the process in accordance with the invention there are broken down in the stone nut shells the bonds between the lignin and the polysaccharides, without the lignin, having to undergo a further polymerisation as it is the case with the known digestion process. The lignin can easily be released from the residue of the filtration of the second stage of the process in accordance with the invention by washing with methanol or acetone. It is then deposited as a yellowish-brownish powder, which is also dissolved by various other solvents. The substance is thermoplastic and very reactive. It serves as a starting material for commercially usable products, such as dyestuffs and pesticides. By pressure treatment with methanol, even further fractions of lignin can be brought in solution.

The residue remaining after the methanol treatment can for example be digested with diluted alkali lye to form cellulose.

The invention is explained by means of the following Example.

EXAMPLE 1,000g husked coconut shells (10% $H_2O$, 29% bound xylose, 6.3% bound acetic acid), are mixed with 1 liter 8% aqueous sodium hydroxide solution (2-molar solution) to form a pulp and allowed to stand for 1 hour at room temperature. Here the temperature of the mixture rises to about 40° C. Now there is added to the mixture 2 liters of water, and kept at boiling temperature for 1 hour. Next the product is absorbed over a filter and the filter cakes are washed neutral $H_2O$. The residue amounts to 770g and contains in addition to 32% bound xylose a further 0.2% bound acetic acid.

770 g (calculated on the dry substance) of the residue are reacted with 2.31 liters 1.0% by weight $H_2SO_4$ and hydrolysed for 1 hour at 135° to 140° C and 2.5 to 4 atmospheres gauge pressure in the agitator autoclave. After absorption and washing with water the residue is 585 g and contains 11.5% pentosane.

The acid filtrate is neutralised with the calculated quantity of calcium carbonate, while stirring, and the gypsum deposit is separated-off.

The xylose solution obtained is desalted with cation and anion exchangers, wherein each liter of cation exchanger and liter of anion exchanger can desalt 12 liters hydrolysate, before the exchangers have to be regenerated. After this the desalted solution is likewise decoloured with cation and anion exchangers, wherein each liter of cation exchanger and liter of anion exchanger can decolour 60 liters of hydrolysate. The ion exchanger capacity thus represents altogether 5 liters hydrolysate for each liter of ion exchanger. From the purified hydrolysate there are obtained 190 g xylose (melting point 144°-146° C), yield 21% in relation to the absolute dry raw material.

COMPARATIVE TESTS

As in the preceding Example there are used 1,000 g husked coconut shells (10% $H_2O$, 29% bound xylose, 6.3% bound acetic acid). Reaction is effected in each case with 3 liters (a) 2.5%, (b) 5%, (c) 7% aqueous caustic soda solution, boiling takes place for 1 hour, filtering is effected and washing as in the Example above. The residue amounts to (a) 862 g, (b) 837 g, (c) 593 g and contains in addition (a) 29%, (b) 30%, (c) 27% bound xylose as well as (a) 3.9%, (b) 1.3%, (c) 0.2% bound acetic acid.

500 g (calculated in respect of the dry substance) of the residue are reacted in each case with 1.5 liters 1.0% by weight $H_2SO_4$ and further processed as in the Example above.

From the purified hydrolysates there are obtained (a) 99 g = 19%, (b) 102 g = 19%, (c) 80 g = 11.1% xylose (melting point 144°-146° C).

The ion exchanger capacity amounts in all to (a) 1.8 liters (b) 2.7 liters (c) 5 liters hydrolysate per liter of ion exchanger.

From the results of the Example and the comparative Examples the following conclusions can be drawn:

(a) The concentration of alkali hydroxide solution is too low with 2.5% NaOH with stone nut shells, to separate-off the bound acetic acid after 1 hour's boiling. The residual content of bound acetic acid still amounts to 3.9%. Although the xylose yield after the acid hydrolysis still amounts to 19% and hence lies only slightly under the yield of the Example (21%) the acid xylose solution is contaminated with acetic acid, which makes itself felt furthermore by the low ion exchanger capacity of 1.8 liters hydrolysate per liter of ion exchanger (in the Example 5 liters hydrolysate per liter of ion exchanger).

(b) Even with an increase in the alkali concentration to 5% NaOH the content of bound acetic acid is still 1.3%, i.e. the acid xylose solution is contaminated with acetic acid. The ion exchanger capacity therefore only amounts to 2.7 liters of hydrolysate per liter of ion exchanger.

(c) After boiling for 1 hour with 7% NaOH solution admittedly the content of bound acetic acid is reduced to 0.2 as in the Example, but the xylose yield after the acid hydrolysis with 11% is only half the yield of the Example.

What is claimed is:

1. In a process for the production of xylose or xylitol wherein a vegetable material is contacted with a basic substance and the solid residue is thereafter treated with an acid, the improvement which comprises:

(a) employing as the vegetable material stone nut shells;

(b) employing as the basic substance a 1.5 to 6 molar alkali metal hydroxide at a temperature of 10° to 50° C.;

(c) thereafter diluting the resultant digestion mass to an alkali metal hydroxide content of no greater than 0.75 molar and further digesting the stone nut shells at a temperature of greater than 60° C.

2. A process according to claim 1 wherein said stone nut shell is the shell of palm nuts, olive stones, date stones, babacu nuts, coconut shells or almond shells.

3. A process according to claim 2 wherein the stone nut shells have a grain size of 1 to 5 mm.

4. A process according to claim 3 wherein the alkali metal hydroxide initally has a concentration of 1.75 to 2.5 molar.

5. A process according to claim 4 wherein the alkali metal hydroxide initally has a concentration of 2 molar.

6. A process according to claim 3 wherein the alkali metal hydroxide at concentrations of 1.5 to 6 molar contact the stone nut shells at a temperature of up to 40° C for ½ to 3 hours.

7. A process according to claim 6 wherein the contacting of the stone nut shells with alkali metal hydroxide of 1.5 to 6 molar is performed for 1 to 2 hours.

8. A process according to claim 6 wherein following dilution of the alkali metal hydroxide the digestion is carried out at the boiling point of the solution under normal pressure.

* * * * *